United States Patent
Crosslin et al.

(12) 
(10) Patent No.: US 6,355,037 B1
(45) Date of Patent: Mar. 12, 2002

(54) APPARATUS AND METHOD OF EXTERNAL SKELETAL SUPPORT ALLOWING FOR INTERNAL-EXTERNAL ROTATION

(75) Inventors: Mari Crosslin, Hernando, MS (US); Anthony James, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/730,176

(22) Filed: Dec. 5, 2000

(51) Int. Cl.$^7$ .............................................. A61B 17/56
(52) U.S. Cl. .............................. 606/57; 606/54; 606/56
(58) Field of Search ............................. 606/57, 53, 54, 606/55, 56, 58, 60, 61, 62, 63, 64, 87, 96, 66, 90, 102, 105

(56) References Cited

U.S. PATENT DOCUMENTS

| | | |
|---|---|---|
| 3,985,127 A | 10/1976 | Volkov et al. |
| 4,338,927 A | 7/1982 | Volkov et al. |
| 4,582,369 A | 4/1986 | Itoh |
| 4,632,573 A | 12/1986 | Itoh |
| 4,751,920 A | 6/1988 | Mauldin et al. |
| 4,950,297 A | 8/1990 | Elloy et al. |
| 5,011,496 A | 4/1991 | Forte et al. |
| 5,074,866 A | 12/1991 | Sherman et al. |
| 5,100,403 A | 3/1992 | Hotchkiss et al. |
| 5,102,411 A | 4/1992 | Hotchkiss et al. |

(List continued on next page.)

FOREIGN PATENT DOCUMENTS

| | | |
|---|---|---|
| EP | 0956836 A1 | 11/1999 |
| GB | 2323037 A | 9/1998 |
| GB | 2324038 A | 10/1998 |
| SU | 986405 | 7/1983 |
| WO | WO98/02116 | 1/1998 |
| WO | WO99/30649 | 6/1999 |

OTHER PUBLICATIONS

Stephan M. Perren, M.D., Ph.D., Jacques Cordey Ph.D., Berton A. Rahn, D.M.D., M.D., Emanuel Gautier, M.D., and Erich Schneider, Ph.D., "Early Temporary Porosis of Bone Induced by Internal Fixation Implants," Clinical Orthopaedics and Related Research dated Nov. 23, 1987, p. 139, No. 232, J.B. Lippincott Company, Philadelphia, Pennsylvania.

(List continued on next page.)

*Primary Examiner*—Pedro Philogene
(74) *Attorney, Agent, or Firm*—Fulbright & Jaworski L.L.P.

(57) ABSTRACT

An external skeletal fixation apparatus provides support about a joint such as the knee. The apparatus includes a first external support section with one or more rings rigidly supporting a first skeletal element (e.g., the femur) on one side of the joint and a second external support section, with two or more rings, rigidly supporting a second skeletal element (e.g., the tibia) on an opposite side of the joint. The apparatus further includes a hinged support section interconnecting the first and second external support sections in the vicinity of the joint such that the hinged support section pivots the joint about a generally lateral axis when the skeletal elements move through angular flexion or extension. The second external support section includes at least a first support ring element and a second support ring element rotatably coupled with the first support ring element. The first support ring element is connected with the hinged support section and the second support ring element is positioned to rigidly support the second skeletal element. Accordingly, the second support element rotates relative to the first support element with generally lateral rotation of the second skeletal element relative to the first skeletal element or the joint.

33 Claims, 6 Drawing Sheets

U.S. PATENT DOCUMENTS

| | | |
|---|---|---|
| 5,121,742 A | 6/1992 | Engen |
| 5,133,758 A | 7/1992 | Hollister |
| 5,277,698 A | 1/1994 | Taylor |
| 5,370,699 A | 12/1994 | Hood et al. |
| 5,397,322 A | 3/1995 | Campopiano |
| 5,549,686 A | 8/1996 | Johnson et al. |
| 5,658,342 A | 8/1997 | Draganich et al. |
| 5,702,458 A | 12/1997 | Burstein et al. |
| 5,702,466 A | 12/1997 | Pappas et al. |
| 5,824,100 A | 10/1998 | Kester et al. |
| 5,824,103 A | 10/1998 | Williams |
| 5,871,543 A | 2/1999 | Hofmann |
| 5,954,770 A | 9/1999 | Schmotzer et al. |
| 6,010,534 A | 1/2000 | O'Neil et al. |
| 6,039,764 A | 3/2000 | Pottenger et al. |

OTHER PUBLICATIONS

John E. Herzenberg, M.D., F.R.C.S.C., James R. Davis, D.O., Dror Paley, M.D., F.R.C.S.C., And Anil Bhave, M.S., P.T., "Mechanical Distraction for Treatment of Severe Knee Flexion Contractures," Clinical Orthopaedics and Related Research, dated Apr., 1994, pp. 80–88, No. 301, J.B. Lippincott Company, Philadelphia, Pennsylvania.

O.V. Oganesyan, M.D., I.S. Istomina, and V.I. Kuzmin, "Treatment of Equinocavorvarus Deformity in Adults with the Use of a Hinged Distraction Apparatus," The Journal of Bone Joint Surgery, dated Apr., 1996, pp. 546–556, vol. 78–A, No. 4, The Journal of Bone and Joint Surgery, Incorporated.

Randall R. Wroble, M.D., Edward S. Grood, Ph.D., and John S. Cummings, M.S., "Changes in Knee Kinematics After Application of an Articulated External Fixator in Normal and Posterior Cruciate Ligament—Deficient Knees," Anthroscopy: The Journal of Arthroscopic and Related Surgery, vol. 13, No. 1 (Feb.), dated 1997: pp. 73–77, Anthroscopy Association of North America.

Peter T. Simonian, M.D., Patrick S. Sussman, M.S., Thomas L. Wickiewicz, M.D., Robert N. Hotchkiss, M.D., Russell F. Warren, M.D., "The Skeletally Fixed Knee Hinge for the Grossly Unstable Knee," The American Journal of Knee Surgery, dated Summer 1998/vol. 11, No. 3, pp. 181–187.

Peter T. Simonian, M.D., Thomas L. Wickiewicz, M.D., Robert N. Hotchkiss, M.D., and Russell F. Warren, M.D., "Chronic Knee Dislocation: Reduction, Reconstruction, and Application of a Skeletally Fixed Knee Hinge," The American Journal of Sports Medicine, vol. 26, No. 4, pp. 591–596, American Orthopaedic Society for Sports Medicine 1998.

Henning Windhagen, Stefan Kolbeck, Hermann Bail, Arno Schmeling and Michael Raschke, "Quantitative Assessment of In–Vivo Bone Regenerate Consolidation in Distraction Osteogenesis," dated Apr. 23, 1999, Department of Orthopaedic Surgery, Hannover Medical School, Hannover Germany; Department of Trauma Surgery, Charité, Humboldt–University Berlin, Berlin, Germany.

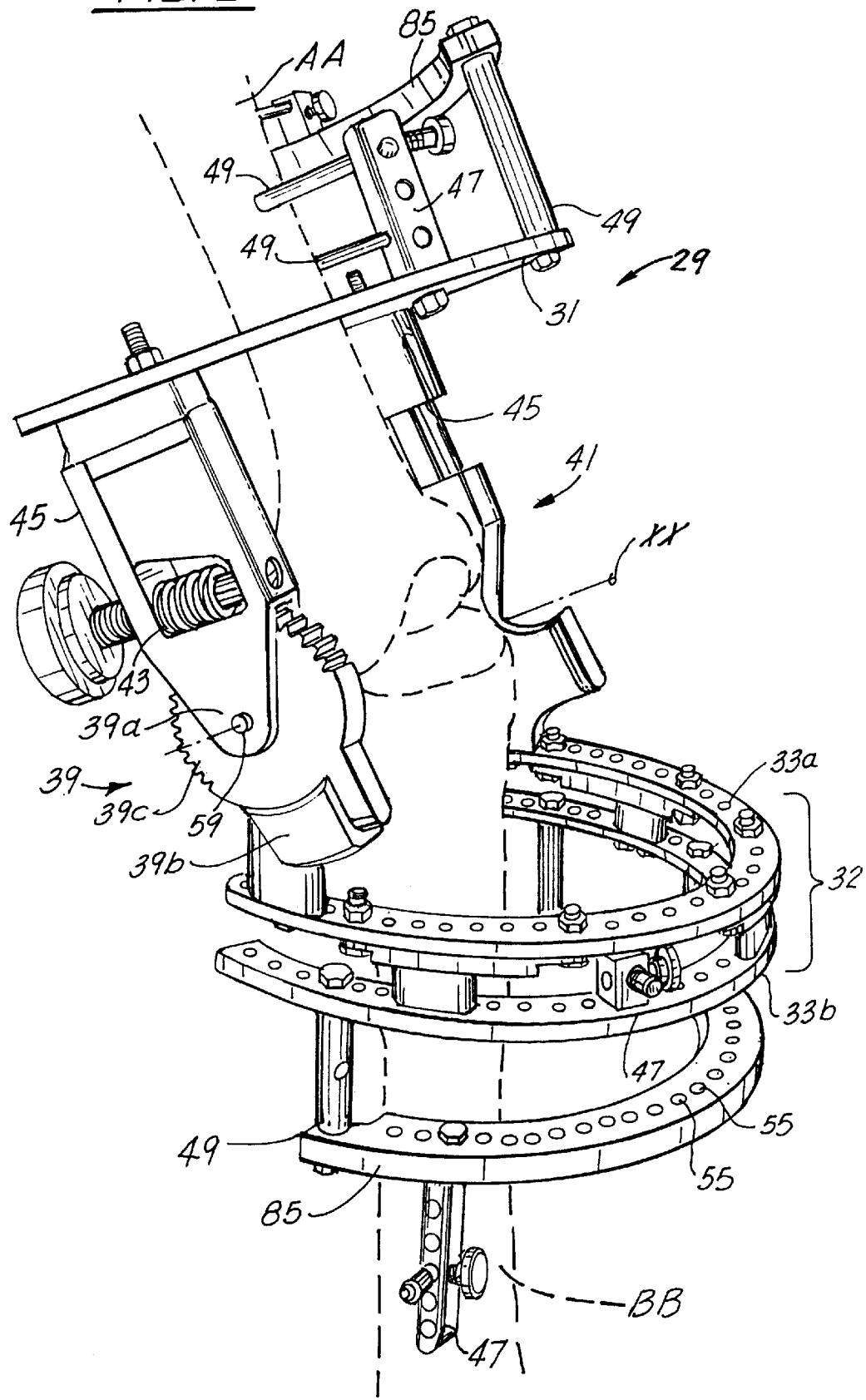

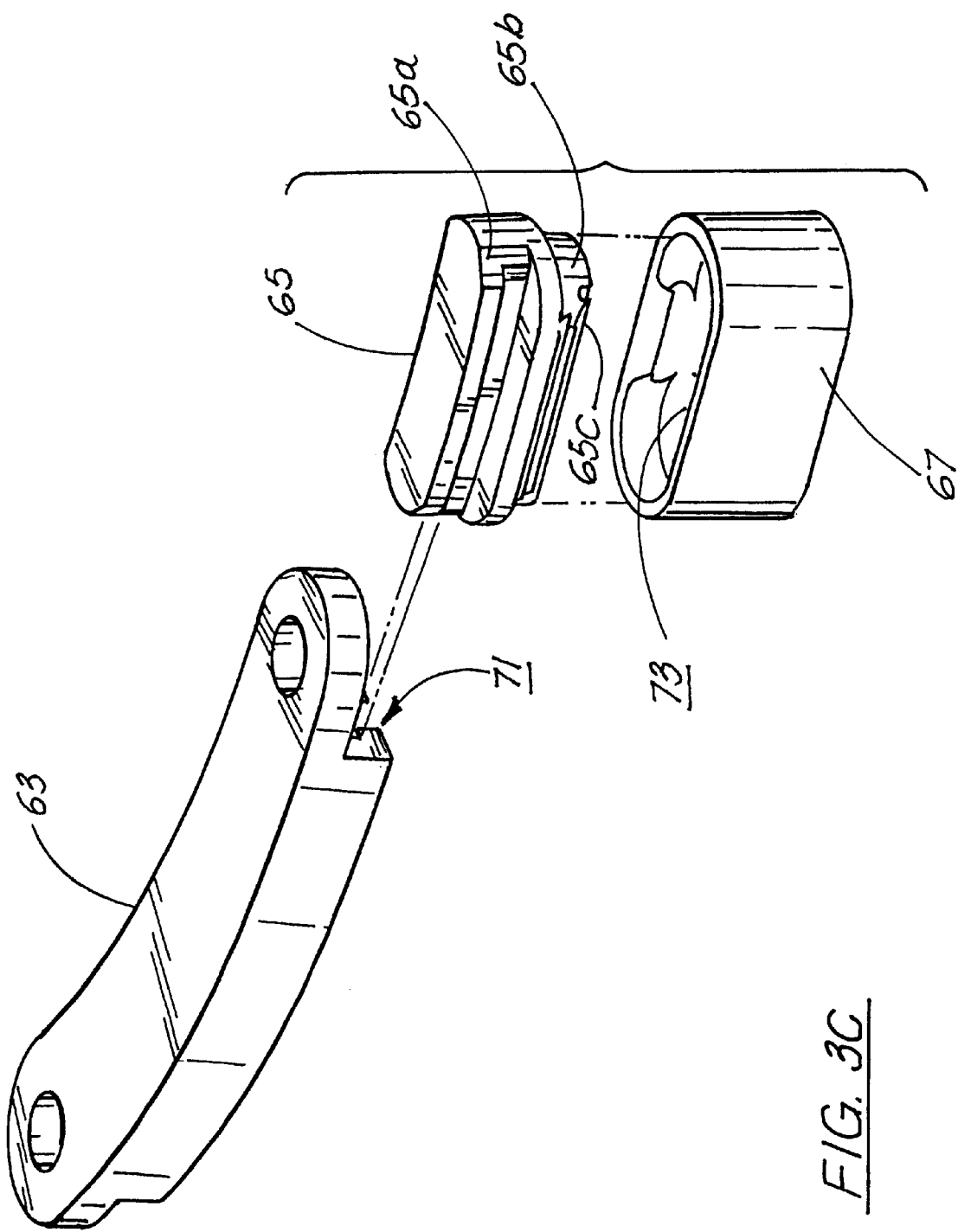

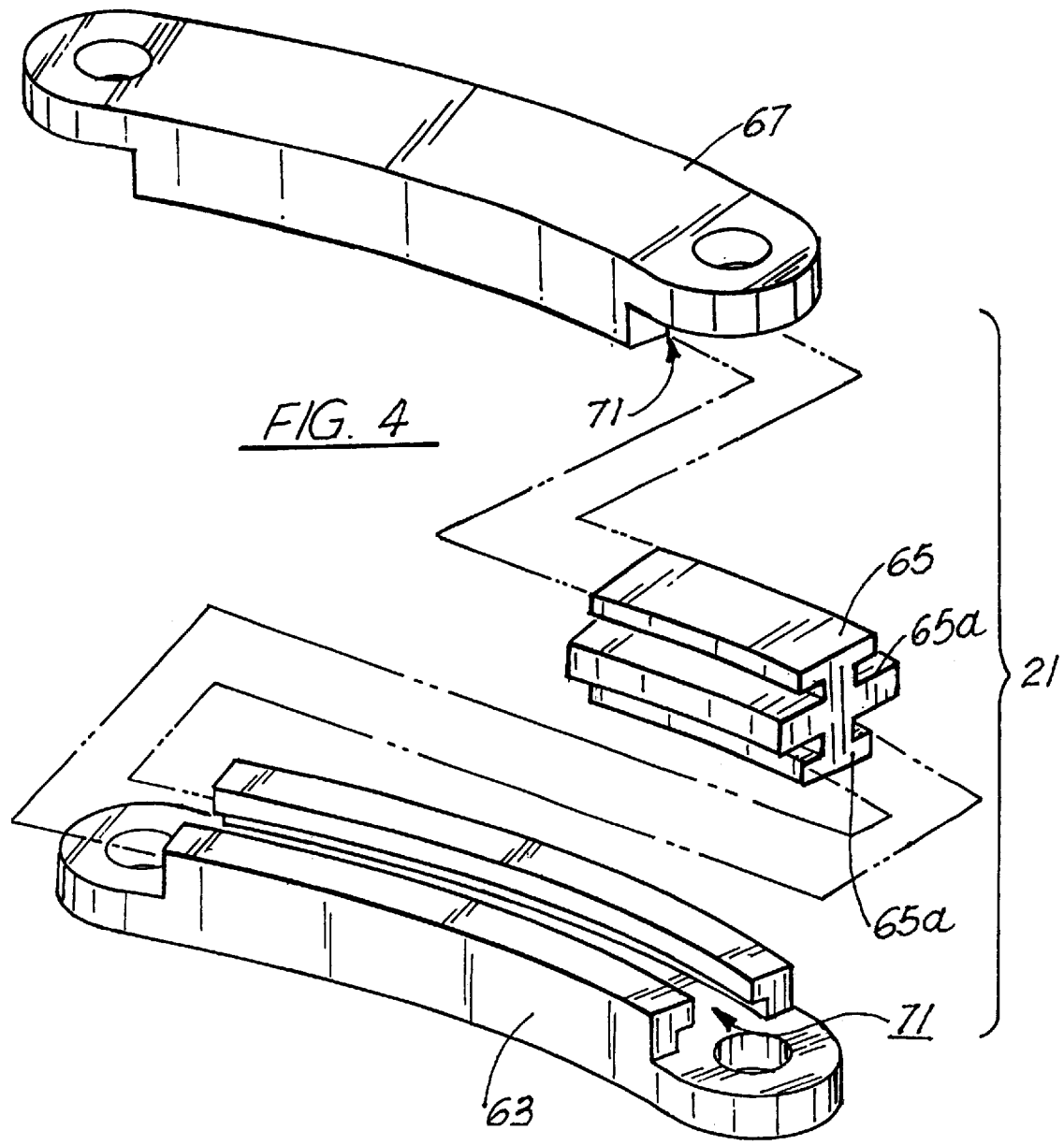

APPARATUS AND METHOD OF EXTERNAL SKELETAL SUPPORT ALLOWING FOR INTERNAL-EXTERNAL ROTATION

BACKGROUND OF THE INVENTION

The present invention relates generally to an apparatus and method of external skeletal support. More particularly, the invention relates to such an apparatus and method of external skeletal support (e.g., through in-vivo fixation) having a component for angular rotation (e.g., knee flexion and extension) and a skeletal support component for relative lateral rotation (e.g., tibial external-internal rotation). Several embodiments of the apparatus and method are particularly adapted for skeletal fixation of skeletal elements and/or for bridging a knee joint or similar joint or ligaments, and in the treatment of tibial fractures and flexure contractures.

The repair of traumatized bone or ligaments is sometimes accomplished through the use of an external skeletal fixation apparatus which includes a number of curved rings or curved semi- or half-rings (referred to collectively herein as "rings" or "ring elements"). The rings are positioned generally about the bone or ligaments (hereinafter "skeletal elements") and spaced apart (i.e., along the longitudinal axis of the bones(s) being treated or supported), but structurally connected via, for example, a plurality of tie rods. In this way, several rings and several tie rods may be used by the surgeon to create an overall frame about the patient's arm, leg or ankle. Further, pins or wires may be fixed to the rings and extend transversely therefrom into the bones, so that the frame and pins support and/or load the bone tissue in a desired manner. Such a system and method has been referred to in the art as the "Ilizarov Technique." The Ilizarov Technique is described generally in U.S. Pat. No. 4,615,338, issue to Gavril A. Ilizarov et al., hereby incorporated by reference. An improvement to the Ilizarov Technique is described generally in U.S. Pat. No. 5,074,866, issued to Sherman et al., on Dec. 24, 1991, also hereby incorporated by reference.

One application to which the present invention is particularly adapted is the treatment of knee and ligament damage, tibial fractures and flexure contractures. External skeletal fixation for these purposes allow for the flexion or extension of the knee (i.e, angular rotation of the tibia relative to the femur) but do not typically allow for lateral rotation of the tibia (i.e., internal-external rotation relative to the knee or femur). Prior art skeletal support methods which provide for internal-external rotation of the tibia relative to the femur have done so through the use of bracing and other ex-vivo skeletal support elements. Although these support elements often provide adequate support for the damaged skeletal element, these do not positively fixate the skeletal element, as would the use of certain in-vivo connector elements such as pins. As an example, U.S. Pat. No. 4,751,920 discloses a pivoting knee brace with rotating and translating tibia collars. The brace is secured to the tibia and femur via straps, with collars positioned around the upper leg and the lower leg and connected via a connecting rod. A series of cams is also provided to control the internal-external rotation of the tibia relative to the femur.

Another skeletal support apparatus referred to as an orthotic device is disclosed generally in U.S. Pat. No. 5,121,742 ("lower extremity orthotic device"). The orthotic device allows the patient to have pivotal knee rotation by employing straps around the thigh and around the calf, and knee joints interspaced between the thigh and calf side numbers. The knee joints are interconnected with the straps by a cable system which allow the knee to be placed in the locked or unlocked position, by utilizing a cable system interconnecting the components of the device.

SUMMARY OF THE INVENTION

It is one of multiple objects of the present invention to provide an external skeletal support apparatus or fixation apparatus that allows for lateral or external-internal rotation of one skeletal element(e.g., the tibia) relative to an interconnected second skeletal element (e.g., femur). It is a further object of the invention to provide such an external skeletal apparatus or fixation apparatus to bridge a joint between two skeletal elements allowing for and supporting angular rotation about the joint (e.g., knee flexion and extension) and lateral rotation of one skeletal element relative to the joint or other skeletal element (e.g., internal-external rotation of the tibia).

Generally, an external skeletal support apparatus according to the invention supports relative movement between at least two skeletal elements (e.g., a femur and tibia). The apparatus includes a first external support section for rigidly supporting a first skeletal element, a second external support section for rigidly supporting a second skeletal element, and a hinged support section interconnecting the first and second external support sections such that the hinged support section pivots to support and/or control the joint through angular rotation (e.g., knee flexion or extension) and/or relative rotation between the two skeletal elements. The second external support section includes at least a first support element and a second support element, which are rotatably coupled such that the second support element is positioned to rigidly support the second skeletal element and is rotatable relative to the first support element with generally lateral rotation of the second skeletal element (e.g., external-internal rotation of the tibia).

In one application, an external skeletal fixation apparatus is provided to support a joint such as the knee joint. The apparatus includes a first external support section rigidly supporting a skeletal element on one side of the joint and a second external support section rigidly supporting a skeletal element on an opposite side of the joint. Further, a hinged support section interconnects the first and second external support sections in the vicinity of the joint such that the hinge support section pivots the joint about a generally lateral axis when the joint is rotated through flexion or extension. The second external support section includes at least a first support ring element and a second support ring element rotatably coupled with the first support ring element. The first support ring element is rigidly connected with the hinged support section and the second support ring element rigidly supports the second skeletal element such that the second support ring element is rotatable relative to the first support element with generally lateral rotation of the second skeletal element relative to the first skeletal element or the joint. Connector pins are preferably used in the support sections to fixedly attach ring element in-vivo with the skeletal element.

Moreover, at least one coupler is preferably used to dynamically couple the second support ring element with the first support ring element such that the second support ring element is rotatable relative to the first support ring element along a predetermined arc path. In one embodiment, the coupler includes a base component having a guide rail and fixedly attached to one of the first and second support ring elements. A slider component is also provided for fixedly attaching to the other support ring element and for slidably engaging the guide rail. The slider component may include a slider block attachable with one support ring element and a slider insert having a first portion lockingly connected with said slider block and a second portion slidably engageable with the rail. Alternatively, the slider block and insert may be formed integrally as a one-piece metallic component.

Compared with known skeletal fixation devices, the inventive fixation apparatus provides for a fixation method that more effectively, and to a greater extent, restores natural mobility. The apparatus is more convenient and comfortable to use and enhances the healing process. Alternatively, compared with known ex-vivo types of skeletal support devices, the skeletal support apparatus according to the invention also provides better support and comfort, and thus, is more effective in enhancing the healing process.

These and other objects, features, and advantages of the present invention will become apparent to those skilled in the art from the following detailed description of one or more preferred embodiments and the accompanying drawings.

BRIEF DESCRIPTION OF THE DRAWINGS

FIG. 2 is a perspective side view of an external skeletal fixation apparatus according to the invention shown in an angularly rotated position;

FIG. 3C is a reversed disassembled view of a slider block and insert for the coupler in FIG. 3;

FIG. 4 is a perspective exploded view of a coupler according to a third embodiment of the invention.

DETAILED DESCRIPTION OF THE PREFERRED EMBODIMENT

Figure 1:
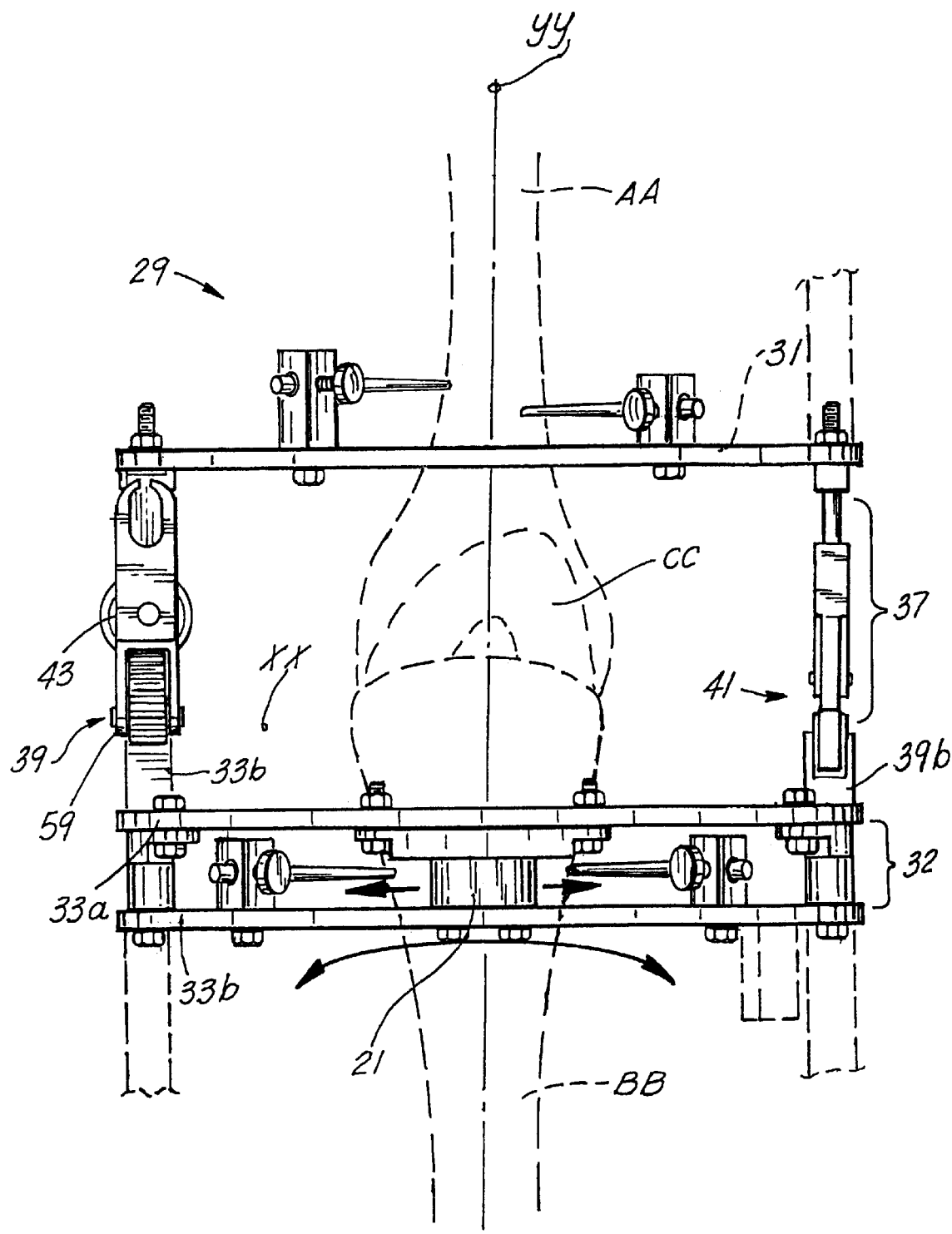
FIG. 1 is a front view of an external skeletal fixation apparatus according to the invention shown applied as a bridge for the knee joint.

FIGS. 1 and 2 depict an external skeletal fixation system or apparatus 29 embodying the invention. The external skeletal fixation apparatus 29 illustrated is particularly adapted for use about or as a bridge for the knee joint CC or to otherwise restore motion to the knee (allowing for and supporting flexion and extension). The present description is, therefore, particularly directed to such an application, although it will become apparent to one skilled in the art that various aspects of the invention are also adopted for alternative applications (including for tibial plateau fractures, flexure contractures, and treatment of other joints of the body).

The apparatus 29 is fixedly attached by stainless steel half-pins 49 to the femur AA and to the tibia BB, and allows for and supports relative motion between the femur AA and tibia BB (as further explained below). In alternative embodiments, the apparatus 29 maybe attached to or about the skeletal element (e.g., femur or tibia) ex-vivo rather than in-vivo (e.g., utilizing straps or bracing). In one aspect of the invention, the fixation apparatus 29 according to the invention also allows for natural lateral or external-internal rotation of the tibia, relative to the femur BB and knee CC.

As shown in the Figures, the apparatus 29 provides a frame positionable about the femur AA, knee CC, and tibia BB. The apparatus 29 may be described as including three support sections. First, a femoral ring 31 (shown as a semi-ring, etc.) is disposed above the knee CC, proximate the femur AA and fixedly attached thereto. Secondly, the apparatus 29 includes a tibial ring construct 32 comprised of one or more tibial rings 33 generally disposed below the knee CC. The tibial ring construct 32 is fixedly attached to the tibia BB and provides support therefor. Thirdly, the apparatus 29 incorporates a universal hinge construct 37 interconnecting the femoral ring 31 with the tibial ring construct 32. Preferably, the universal hinge construct 37 is, for the illustrated application, a universal hinge system commercially available from Smith & Nephew, Inc., Memphis, Tenn., under the trademark COMPASS.

The hinge construct 37 includes a universal hinge 39 and a slave hinge 41 disposed in parallel relation and generally circumferentially opposite each other (and thus, normally on opposite sides of the knee). Generally, the hinge construct 37 is used to control distraction and rotation of the joint, thereby restoring, maintaining, or increasing the range of motion of the joint.

Specifically, the hinges 39, 41 of FIGS. 1 and 2 function to bridge the knee CC and to control and support relative angular motion between the femoral ring 31 and the tibial ring construct 32. Such lateral motion is provided about a lateral axis XX generally extending through the center of the knee CC. As illustrated in the Figures, lateral axis XX is a mechanical center line or axis of the apparatus 29 that extends through pivots 59 of the pair of hinges 39, 41. FIG. 2 illustrates the apparatus 29 in a slightly bent or angularly rotated position, and with additional rings and pins provided to further support the skeletal elements at multiple locations and angles.

The universal hinge construct 37 extends between the rings 31, 32 and includes a master universal hinge 39 and a slave hinge 41. Each of hinges 39, 41 is equipped with a telescoping mechanism 45 which allows adjustment of the height of the apparatus. Each hinge 39,41 includes a pivoting plate 39a that is pivotable about a base 39b and about the pivot 59. The base plate 39b is typically provided with bolt holes such that the hinge construct 37 may be positioned at a various locations along the circumference of the rings. The master universal hinge 39 is further equipped with a ratcheted wheel 39c that is operable with an adjustable precision worn gear 43 disposed thereabove. The universal hinge construct 37 is therefore angularly adjustable as well as vertically adjustable.

The femoral ring 31 is attachable by bolts and the like to the top of the hinges 39, 41. Referring specifically to FIG. 2, the rings 31 and 33 are equipped with circumferentially spaced lateral holes 55 which are adapted for securement of cubed pin adapters 47. The adapters 47 come in a variety of sizes (i.e., heights) and are equipped with holes for attachment of the half-pins 49. Placement of the apparatus requires one end of the half-pins 49 to be secured to the adapters 47 and the opposite end directly attached (i.e., in-vivo) to the skeletal element. The ring 31 may also accommodate a ring extension post 49 to interconnect the ring 31 with another, accessory ring 85 such as depicted in FIG. 2. Such an accessory ring 85 may be used to support additional assemblies of adapters 47 and pins 49 for attachment to the bone. Accordingly, the system of rings, adapters, and extension posts provide a large degree of flexibility in the placement of the pins with the bone at various angles and locations.

The tibial ring construct 32 of the invention may include two or more rings 33. The tibial ring construct 32 includes a first ring 33a disposed proximate the knee and the rest of the apparatus 29, and a second or bottom tibial ring 33b disposed on the distal side of the tibial ring 33a. In one aspect of the invention, the tibial ring 33b is fixedly attached to the tibia BB, but rotatably attached to the tibial ring 33a so as to allow relative motion therebetween. Specifically, the tibial ring 33b is dynamically coupled to tibial ring 33a so as to allow relative rotatable motion between the rings 33a, 33b and between the tibia BB and the femur AA or knee CC. Such relative motion is provided through use of one or more inventive coupler mechanisms or couplers 21 which couple or attach tibial ring 33a with tibial ring 33b. The bottom tibial ring 33b, being fixedly attached to the tibia BB, allows for and supports external and internal rotation with the tibia BB, while top tibial ring 33a remains stationary and fixed to the rest of the apparatus 29. The tibial construct 32 of FIGS. 1 and 2 is shown utilizing at least three dynamic couplers 21.

The tibial rings 33a, 33b are disposed in parallel relation and vertically spaced by one or more of the couplers 21. As shown above, additional rings or semi-rings may be attached, by way of ring extension posts 49, to the bottom tibial ring 33b and to the tibia BB, so as to be rotatable with the bottom tibial ring 33a. Further, additional cube pin adapters 47 may be provided with these additional rings for support of a pin 49 attachable with the tibia BB.

Figure 5:
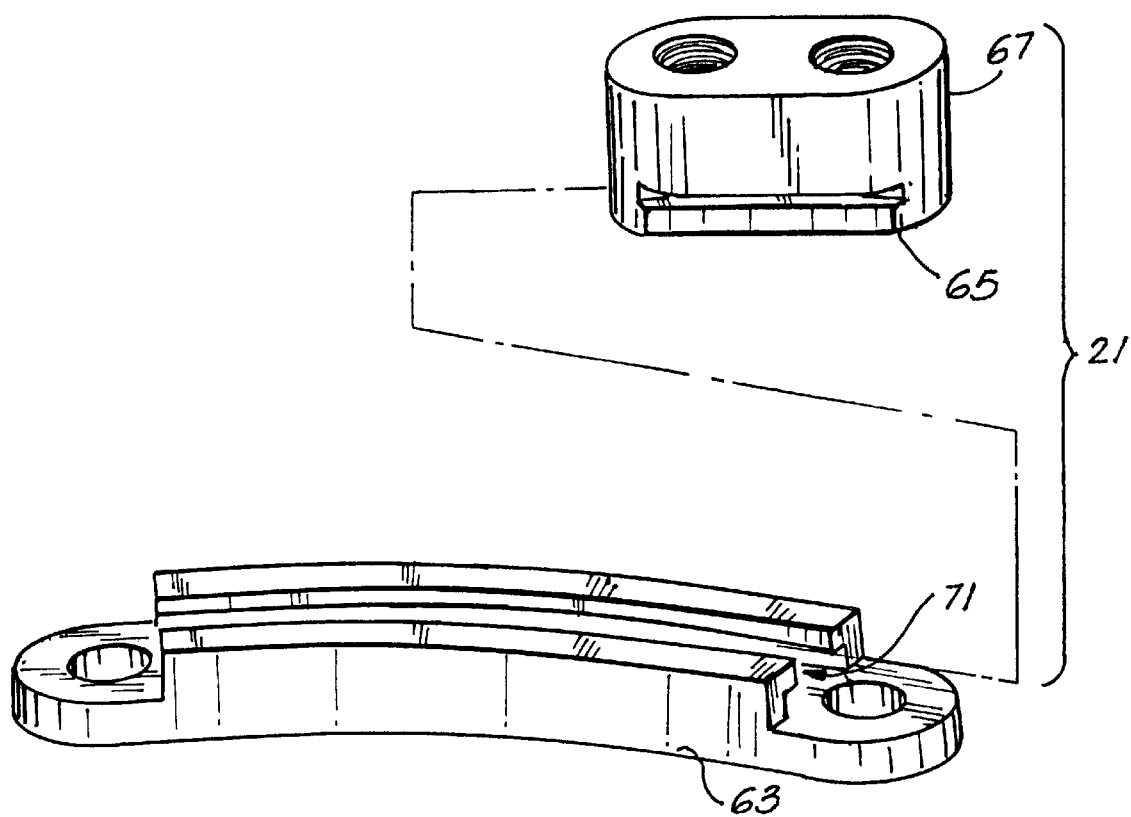
FIG. 5 is a perspective view of a coupler according to a fourth embodiment of the invention.

Each of FIGS. 3–5 depict various coupler mechanisms or couplers 21 according to the invention and applicable to an external skeletal fixation apparatus also according to the invention, wherein like elements are indicated by like reference numerals. Each of these couplers 21 includes a first component attachable to tibial ring 33b (and thus movable therewith), and a second component attachable with fixed tibial ring 33a (and thus movable therewith). The two components are generally dynamically engaged or coupled such that the one component is moveable relative to the other component about a prescribed, predetermined path. In these embodiments, such a path is arc-shaped and corresponds with the curvature of the tibial rings 33a, 33b. In this way, the tibial rings 33a and 33b are rotatable relative to each other along a predetermined arc length. Also in this manner, the tibial ring 33b is allowed to externally-internally rotate with the natural motion of the tibia and relative to the rest of the apparatus 29 (including tibial ring 33) which is fixed to the femur AA. Preferably, the couplers 21 are designed to allow for up to 20 degrees relative rotation of the rings.

It should be noted that in each of the embodiments of FIGS. 3–5, the coupler 21 is an assembly of two or more components which are interchangeable such that any one component may be alternately fixed to the tibial ring 33a or tibial ring 33b. Moreover, these couplers 21 may be adapted for use with external support apparatuses other than the apparatus 29 of FIGS. 1 and 2. Such modifications will become apparent to one skilled in the art upon review of the present description and/or the accompanying drawings.

Figure 3A:
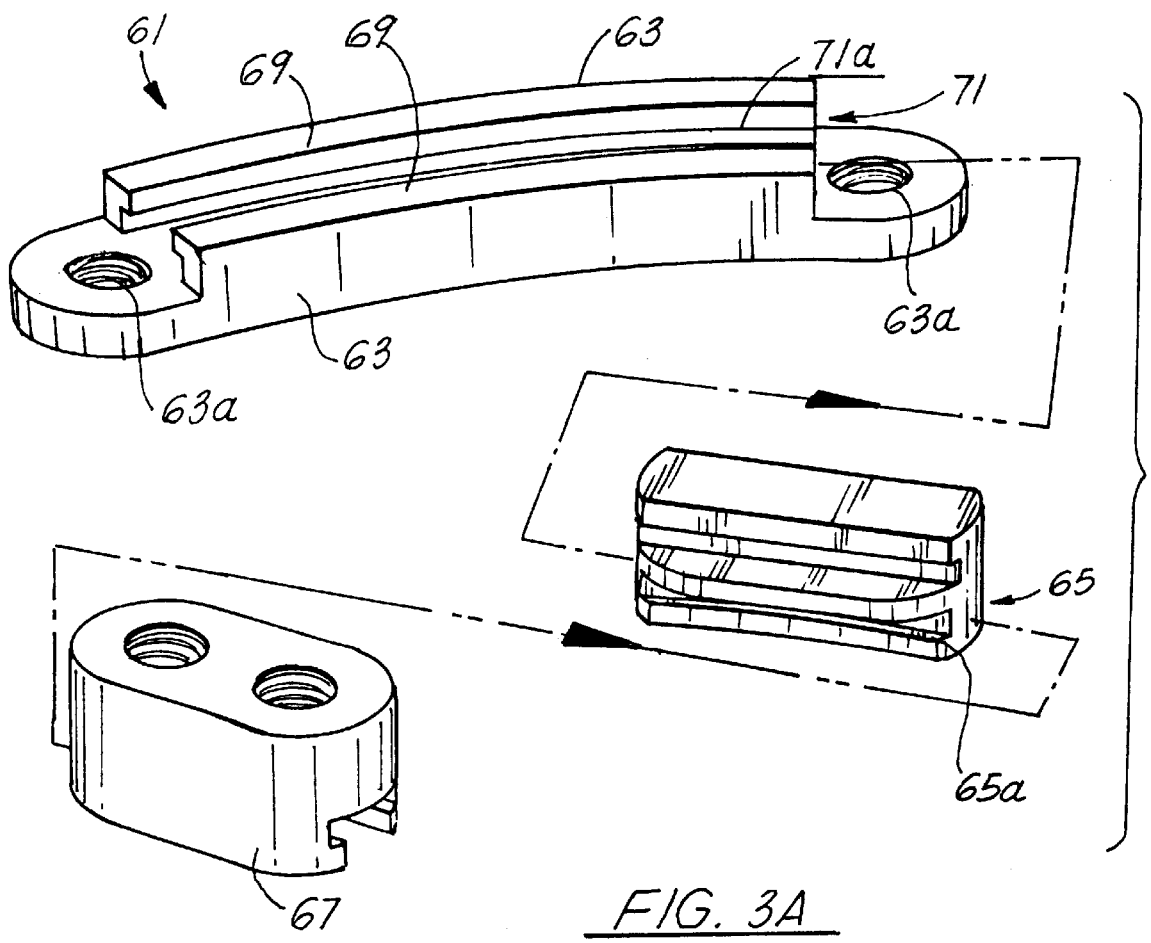
FIG. 3A is a perspective exploded view of a dynamic coupler according to one embodiment of the invention.
Figure 3B:
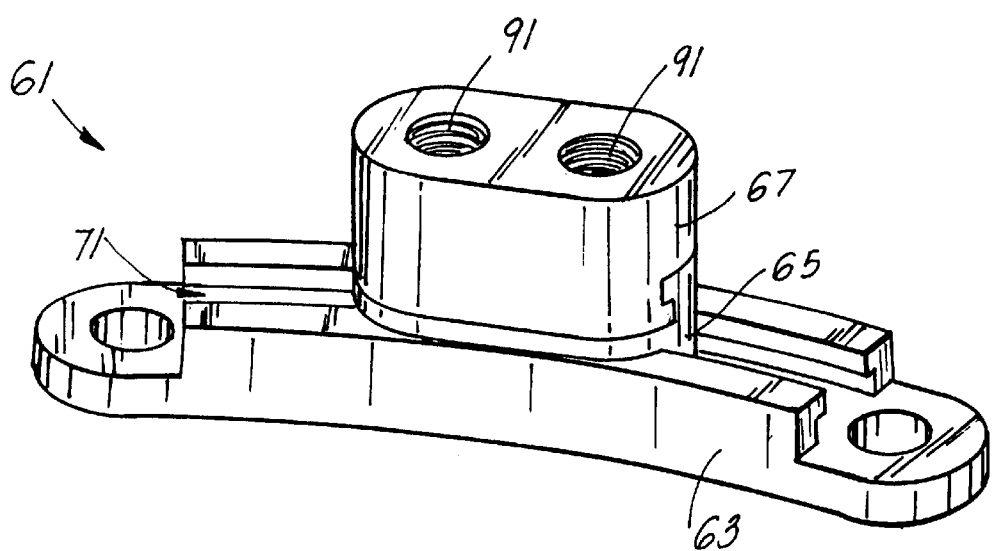
FIG. 3B is a perspective view of the coupler in FIG. 3A shown assembled.

FIGS. 3A–3C depict a three-piece "snap-in slider" assembly for coupler 21. The coupler 21 includes a base plate 63 attachable to one ring, a slider block 67 attachable to the corresponding ring, and a bearing surface slider insert 65 attachable between the base plate 63 and the slider block 67. With reference to the skeletal fixation apparatus of FIGS. 1 and 2, the base plate 63 is bolted to the tibial ring 33b, while the slider block 27 is attached to the tibial ring 33a. The base plate 23 is provided with two bolt holes 23a for connecting with the tibial ring 33b. Similarly, slider block 67 is provided with two threaded blind holes 91 for attachment with the tibial ring 33a.

The base plate 63 is preferably an elongated, arc-shaped structure having a raised platform 69 that defines a slotted guide rail 71. The rail 71 of FIG. 3 may be described as an elongated, slotted channel having an upside down "T" cross-section (which provides the female portion of the interlocking coupler). The arc length of the rail 71 may extend up to about 20° and is designed to correspond with the desired (natural) lateral rotation of the tibia BB. Further, the arc of the rail 71 is designed to correspond with the size of the tibial rings 33a, 33b. Note that the two bolt holes 63a of the base plate 63 is positioned so as to match the hole pattern of the tibial ring 33a. Accordingly, the arc of the rail 71 also defines the center of rotation of the tibial rings 33a, 33b. FIG. 3B depicts the three-piece coupler 21 assembled, with the slider insert 65 permanently fit to the slider block 67.

Preferably, the slider insert 65 is a polyethylene component having a bottom portion 65a shaped to accommodate or correspond with the T-shaped rail 71. Providing the male portion of the interlocking coupler 29, the bottom portion 65a of the insert 65 vertically interlocks with the rail 71 but so as to be laterally slidable therein. Further, the upper portion 65b of the insert 65 is specifically shaped so as to be pressed fit into a recessed female portion 73 on the underside of slider block 67 (see FIG. 3C). Preferably, the upper portion 65b is equipped with dove-tailed, flexible lips 65c that is easily engageable with corresponding ledges on the rail 71, and so as to lockingly engage the slider insert 65 with the slider block 67. The slider block 67 and the insert 65 are designed to permanently interlock, such that they cannot become disassembled in use. However, it should be understood that other interlocking mechanisms known in the art could be adapted for application in these coupler embodiments. FIG. 3B illustrates the positioning of the slider block 67 in locking engagement with the rail 71.

FIG. 4 illustrates yet another three-piece design of the inventive coupler 21 which may be referred to as a "double slide" design. Each of the base plate 63 and the slider block 67 is provide with a "T"-shaped, slotted guide rail 71. The inventive slider insert 65 is therefore provided with double "T"-shaped drawer portions 65a slidable in and corresponding with rails 71.

FIG. 5 depicts a two-piece variation or assembly of the inventive coupler 21. The coupler 21 includes a base plate 63 that is substantially similar to the base plate of FIG. 3. But, the slider block 67 and slider insert 65 form a one-piece, preferably metallic construction. The one-piece construction includes slider insert portion 65 that is formed integrally with the slider block portion 67.

The above designs provide just a few examples of design variations which will become apparent to one skilled in the art upon reading the description and viewing the accompanying drawings. For example, any of the couplers of FIGS. 3–6 may be may be modified to incorporate a roller bearing mechanism and/or a linear rail track (e.g, such as that commercially available from Tsubaki and referred to in U.S. Pat. Nos. 4,582,369 and 4,632,573, both of which are hereby incorporated by reference). Further variations and modifications, to the inventive coupler 29 or to other components of the external skeletal fixation apparatus, or their use, will also become apparent to one skilled in the relevant medical or mechanical art having access to the present description and/or drawings.

The systems, apparatuses, and methods described herein are particularly adapted for external fixation of the knee. However, it will be apparent to one skilled int the art, upon reading the description and viewing the accompanying drawings, that various aspects of the invention are also applicable in other systems for skeletal fixation. For example, the external fixation apparatus and method, or certain aspects of the apparatus and method, may be adapted for fixation of the elbow, ankle, and other bones, ligaments, and joints.

Thus, the foregoing description is presented for purposes of illustration and description, and is not intended to limit the invention to the forms disclosed herein. Consequently, variations and modifications commensurate with the above teachings and the teachings of the relevant art are within this corporate invention. Such variations will readily suggest themselves to those skilled in the relevant mechanical, medical and/or orthopedic art, and are encompassed within the spirit of the invention and the scope of the following claims. Further, the embodiments described are also intended to explain the best mode for practicing the invention, and to enable others skilled in the art to utilize the invention and such, or other, embodiments, and with various modifications required by the particular applications or uses of the invention. It is intended that the appended claims be construed to include alternative embodiments to the extent that is permitted by prior art.

What is claimed is:

1. An external skeletal support apparatus for supporting relative movement between skeletal elements, said apparatus comprising:
    a first external support section for rigidly supporting a first skeletal element disposed generally on one side of a joint;
    a second external support section for rigidly supporting a second skeletal element disposed generally on the opposite side of the joint; and
    a hinged support section interconnecting said first and second external support sections such that said hinged support section pivots to support the joint through angular rotation; and
    wherein said second external support section includes at least a first support element connected with said hinged support section and a second support element rotatably coupled with said first support element, said second support element being positioned to rigidly support the second skeletal element such that said second support element is rotatable relative to said first support element with generally lateral rotation of the second skeletal element.

2. The apparatus of claim 1, further comprising:
    one or more first connectors fixedly attached in-vivo between said first external support section and the first skeletal element; and
    one or more second connectors fixedly attached in-vivo between said second support element of said second external support section and the second skeletal element.

3. The apparatus of claim 1, wherein said second external support section includes a coupler dynamically coupling said second support element with said first support element such that said second support element is rotatable relative to said first support element.

4. The apparatus of claim 3, wherein said coupler dynamically couples said first and second support elements to guide said second support element through relative rotation along a predetermined path corresponding with the rotational path of the second skeletal element.

5. The apparatus of claim 3, wherein said coupler includes a first component attached to one of said first and second support elements, said first component having an arc-shaped rail, and a second component attached to said other support element, said second component being slidably engageable with said rail to direct relative rotation between said first and second support elements.

6. The assembly of claim 3, wherein said coupler includes,
    a first component attached to one of said support elements, said first component defining a rail,
    a second component attached to said other of said support elements, and
    an insert component lockingly engaged with said second component and slidably engageable with said rail.

7. The assembly of claim 1, wherein said hinge support section includes a universal hinge adapted to support flexion or extension of the joint.

8. The assembly of claim 1, wherein each of said first and second external support sections includes one or more rings fixedly attachable by connector pins with one of the skeletal elements to provide support therefor.

9. The assembly of claim 1, wherein said hinge support section is adapted for bridging a knee joint and for allowing angular rotation thereof.

10. The assembly of claim 9, wherein said second external support section is adapted for in-vivo fixation with the tibia and for supporting external-internal rotation of the tibia.

11. A coupler for dynamically coupling a first support ring to a second support ring of a first support section of an external skeletal fixation apparatus, wherein the fixation apparatus is adapted to bridge a joint between a first skeletal element and a second skeletal element so as to support angular rotation of the joint and to fixedly attach each of the two support sections in-vivo with one of the skeletal elements, said coupler comprising:
    a base component attachable to a first support ring, said base component having a guide rail; and
    a slider component attachable to a second support ring spaced vertically from the first support ring, said slider component having an insert portion slidably engageable with said rail to provide relative rotation between the first support ring and the second support ring while supporting lateral rotation of the second skeletal element.

12. The coupler of claim 11, wherein said slider component includes,
    a slider block attachable to the second support ring, and
    an insert permanently lockingly engaged with said slider block, said insert having a male insert portion slidingly engageable with said rail.

13. The coupler of claim 11, wherein said insert portion is integrally formed as one-piece with a slider block body of said slider component.

14. The coupler of claim 11, wherein said insert portion is formed from a metal.

15. The coupler of claim 11, wherein said insert portion is formed from a polyethylene material.

16. An external skeletal fixation apparatus providing support about a joint, said apparatus comprising:
    a first external support section rigidly supporting a skeletal element on one side of the joint;
    a second external support section rigidly supporting a skeletal element on an opposite side of the joint;
    a hinged support section interconnecting the first and second external support section in the vicinity of the joint such that said hinge support section pivots the joint about a generally lateral axis when the skeletal elements move through flexion or extension; and wherein said second external support section includes at least a first support element and a second support element rotatably coupled with said first support element, said first support element being rigidly connected with the hinged support section and said second support element rigidly supporting the second skeletal element such that said second support element is rotatable relative to said first support element with generally lateral rotation of the second skeletal element relative to the first skeletal element or the joint.

17. The apparatus of claim 16, further comprising:

one or more first connector pins fixedly attached in-vivo between said first external support section and said first skeletal element; and one or more second connector pins fixedly attached in-vivo between said second support element of said second external support section and said second skeletal element.

18. The apparatus of claim 16, wherein said second external support section includes at least one coupler dynamically coupling said second support element with said first support element such that said second support element is rotatable relative to said first support element along a predetermined arcuate path.

19. The apparatus of claim 18, wherein said coupler includes a base component fixedly attached to one of said first and second support elements, said base component having a guide rail, and a slider component fixedly attached to said other support element, said slider component being slidably engageable with said rail.

20. The apparatus of claim 19, wherein said slider component includes a slider block attachable with one of said support elements and a slider insert having a first portion lockingly engaged with said slider block and a second portion slidably engageable with said rail.

21. The coupler of claim 19, wherein said slider component includes a slider block portion attachable with one of said support elements and a slider insert portion integrally formed as one-piece with said slider block portion, said slider insert portion being slidably engageable with said rail to dynamically couple said first and second support elements.

22. The apparatus of claim 18, wherein said coupler dynamically couples said first and second support elements to guide said second support element through rotation along a predetermined path corresponding with the rotational path of the second skeletal element.

23. The apparatus of claim 22, wherein each of said first and second support elements is a ring element.

24. The apparatus offal 16, wherein said hinge support section includes a universal hinge adapted to support flexion and extension of the joint.

25. An external skeletal fixation apparatus disposed to bridge a kneejoint, said apparatus comprising:

a first external support section including a ring element rigidly supporting the femur on one side of the joint and one or more transversely extending pins fixed in-vivo between the femur and said ring element;

a second external support section rigidly supporting the tibia on an opposite side of the joint;

a hinged support section interconnecting the first and second external support section in the vicinity of the joint such that said hinge support section pivots the knee joint through flexion or extension; and wherein said second external support section includes at least a first support ring element and a second support ring element rotatably coupled with said first support ring element, said first support ring element being rigidly connected with the hinged support section and said second support ring element having transversely extending pins fixed in-vivo between the second support ring element and the tibia such that said second support ring element is rotatable relative to said first support ring element to support external-internal rotation of the tibia.

26. The apparatus of claim 25, wherein said second external support section includes at least one coupler dynamically coupling said second support ring element with said first support ring element such that said second support ring element is rotatable relative to said first support ring element along a pre-determined arcuate path corresponding with the arc path of the external-internal rotation of the tibia.

27. The apparatus of claim 26, wherein said coupler includes a base component fixedly attached to one of said first and second support ring elements, said base component having a guide rail, and a slider component fixedly attached to said other support ring element, said slider component being slidably engageable with said rail.

28. The apparatus of claim 27, wherein said slider component includes an insert portion, said insert portion being formed from the group of materials consisting of polyethylene and metal.

29. A method of externally supporting relative movement between skeletal elements disposed on opposite sides of a knee joint, said method comprising the steps of:

assembling an external skeletal support apparatus around the joint, wherein the support apparatus includes a first external support section, a second external support section having a first support element and a second support element, and a hinge support section interconnecting the first and second external support section such that the hinge support section can pivot to support the joint through angular rotation, and wherein the first support element of the second external support section is connected with the hinge support section and the second support element of the second support section is rotatably coupled with the first support element;

using the first external support section to rigidly support a first skeletal element disposed generally on one side of the joint; and using the second external support section to rigidly support a second skeletal element disposed generally on the opposite side of the joint, whereby the second support element rigidly supports the second skeletal element and the second support element is rotatable relative to the first support element with generally lateral rotation of the second skeletal element.

30. The method of claim 29, further comprising the steps of:

rigidly attaching the first external support section in vivo with the femur; and rigidly attaching the second support element of the second external support section in vivo with the tibia.

31. The method of claim 29, further comprising the steps of dynamically coupling the second support element with the first support element such that the second support element is rotatable relative to the first support element; and guiding the second support element through relative rotation along a predetermined arcuate path corresponding with a rotational path of the second skeletal element.

32. The method of claim 29, further comprising the step of providing a universal hinge of the hinge support section to bridge the knee joint and support flexion and extension of the knee joint.

33. The method of claim 32, further comprising the step of rigidly attaching the first support section in vivo with the femur and fixedly attaching the second support element in vivo with the tibia to support external-internal rotation thereof.

* * * * *